US010001486B2

(12) United States Patent
Curry et al.

(10) Patent No.: US 10,001,486 B2
(45) Date of Patent: Jun. 19, 2018

(54) METHOD OF USING DIFFERENTIAL MEASUREMENT IN TWO OR MORE CHANNELS TO IMPROVE SENSITIVITY

(75) Inventors: Bo U. Curry, Loveland, CO (US);
Rene P. Helbing, Loveland, CO (US)

(73) Assignee: Alverix, Inc., Franklin Lakes, NJ (US)

( * ) Notice: Subject to any disclaimer, the term of this patent is extended or adjusted under 35 U.S.C. 154(b) by 507 days.

(21) Appl. No.: 11/500,626

(22) Filed: Aug. 8, 2006

(65) Prior Publication Data

US 2008/0038711 A1    Feb. 14, 2008

(51) Int. Cl.
*C12Q 1/00* (2006.01)
*C12Q 1/68* (2018.01)
*G06F 19/00* (2018.01)
*G01N 33/58* (2006.01)
*G01N 33/558* (2006.01)

(52) U.S. Cl.
CPC ......... *G01N 33/582* (2013.01); *G01N 33/558* (2013.01)

(58) Field of Classification Search
None
See application file for complete search history.

(56) References Cited

U.S. PATENT DOCUMENTS

| 6,235,241 B1* | 5/2001 | Catt ................ B01L 3/5023 |
| | | 422/404 |
| 6,696,240 B1* | 2/2004 | Kloepfer et al. ............ 435/4 |
| 7,223,364 B1* | 5/2007 | Johnston et al. ......... 422/68.1 |
| 2007/0131548 A1* | 6/2007 | Winarta et al. ......... 204/403.02 |

* cited by examiner

*Primary Examiner* — Dirk Bass
(74) *Attorney, Agent, or Firm* — Knobbe, Martens, Olson & Bear LLP

(57) ABSTRACT

A method to calibrate measurements of a test analyte in a test sample including measuring at least one test-light level responsive to reactions of at least one reagent group and at least one reactive test analyte in the test sample and measuring at least one control-light level responsive to reactions of at least one reagent group and at least one control analyte in a control sample. Each control analyte is a known amount of at least one reactive test analyte. The method further includes determining a presence of the reactive test analyte in the test sample based on the measured test-light levels and control-light levels. The reagent group and the reactive test analyte react by attaching to each other.

14 Claims, 14 Drawing Sheets

METHOD OF USING DIFFERENTIAL MEASUREMENT IN TWO OR MORE CHANNELS TO IMPROVE SENSITIVITY

BACKGROUND

Currently, assays are read by human eye or high cost imaging system and the reading of assays are determined by individual human judgment or expensive equipment. The purpose of reading these assays is to determine whether a test sample of biological or chemical material being assayed includes a particular analyte, or a derivative or constituent of the analyte. The particular analyte, which is the subject of the assay, is referred to as a test analyte. The test sample may include biological material such as urine, saliva, blood plasma, or the like. The test sample may include chemical material such as rainwater, sludge, or the like.

An assay is performed using a substrate having a sensitive region patterned on the surface of the substrate. Such substrates may include channels that wick the test sample up and over the sensitive regions patterned within the channels. In some case, the substrate is made of silicon or glass and has a smooth surface. If the substrate includes channels, the channels are etched in the substrate and the sensate region is patterned within the etched channels. In other cases, the substrate is made of paper. If the paper substrate includes channels, the channels are defined by the type and/or density of the paper or by thickness variations in the paper.

The sensitive region reacts to exposure of a test analyte. The sensitive region is indistinguishable from the substrate outside the sensitive region until the sensitive region is exposed to the test analyte. The reaction can be a bonding of the material in the sensitive region with the test analyte. The reaction is detected by an emission of light from the reacted region. In some cases, light is incident on the assay after exposure to a test sample. If a reaction has occurred, some of the incident light is reflected from the bonded material. For example, gold atoms are attached to the test analyte and incident light is reflected from the bound gold atoms. In other cases, if a reaction has occurred, the bonded material fluoresces upon exposure to the incident light.

A human observes the sensitive region to determine if there was a sufficient change in the appearance of the sensitive region relative to the rest of the substrate. When readings to determine an exposure of the sensitive region to of a test analyte are made by the human eye, the readings may not be consistent and may be prone to error. When assays are read by equipment, such as a charge-coupled device (CCD), the determination of an exposure of the sensitive region to of a test analyte may be consistent and relatively error free. However, the equipment typically must be high resolution to make the accurate determination and such equipment is expensive.

In some instances, it is useful to determine the amount of analyte in the test sample. For example, if a physician is treating a physical condition for a patient and the patient's blood is the test sample A market demand exists for a simple, inexpensive system to determine whether a test sample of biological or chemical material being assayed includes a particular analyte, or a derivative or constituent of the analyte. There is also a market demand for quantifying the amount of includes a particular analyte, or a derivative or constituent of the analyte in an inexpensive system.

SUMMARY

The invention provides in a first aspect a method to calibrate measurements of a test analyte in a test sample. The method includes measuring at least one test-light level responsive to reactions of at least one reagent group and at least one reactive test analyte in the test sample, measuring at least one control-light level responsive to reactions of at least one reagent group and at least one control analyte in a control sample. Each control analyte is a known amount of at least one reactive test analyte. The method further includes determining a presence of the reactive test analyte in the test sample based on the measured test-light levels and control-light levels. The reagent group and the reactive test analyte react by attaching to each other.

The invention provides in a second aspect a test strip to calibrate measurements of one or more test analytes in a test sample. The test strip includes at least two channels, each channel including reagent portions having associated reagent groups. Each channel receives either the test sample or a selected control sample. The selected control sample includes a known amount of at least one test analyte and the test sample includes either an unknown amount of at least one test analyte or an undetectable amount of the test analytes.

The invention provides in a third aspect a system to calibrate measurements of one or more test analytes from a test sample. The system includes a photodetector array and a processor communicatively coupled to the photodetector array. The photodetector detects light correlated to at least three reagent portions of a test strip and detects a reference light from at least one blank portion of the test strip. The processor determines reaction light levels correlated to the light detected from each of the reagent portions, determines a reference-light level correlated to the blank portion, forms calibration curves for respective reagent groups based on respective first reaction light levels and respective second reaction light levels and determines an amount of one or more test analytes in the test sample based on placements of third reaction light levels on respective calibration curves.

The invention provides in a fourth aspect a system to calibrate measurements of one or more test analytes in a test sample. The system includes means for measuring test-light levels from reactions of test analytes with reagent groups, means for measuring control-light levels from reactions of control analytes with reagent groups, means for forming calibration curves based on detected control-light levels, and means for determining amounts of the test analytes in the test sample from placements of the test-light levels on the calibration curves.

DRAWINGS

Figure 11:
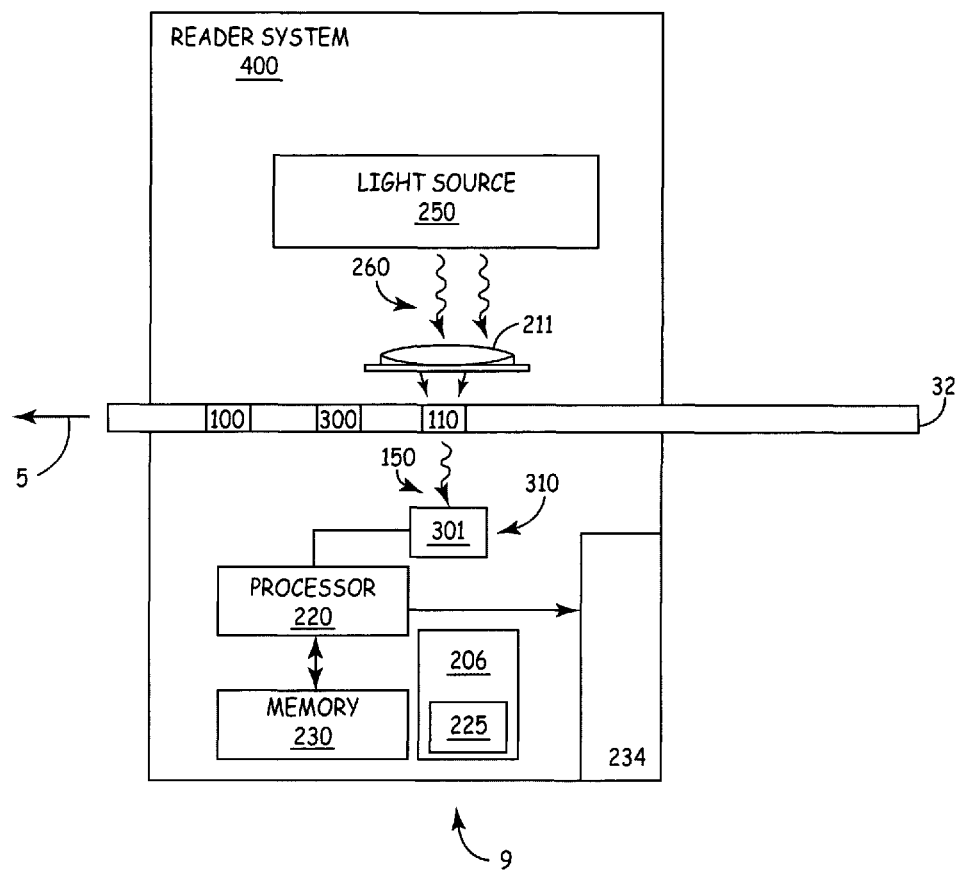

FIG. 11 a cross-sectional side view of one embodiment of a system to calibrate measurements of one or more test analytes from a test sample.

Figure 12A:
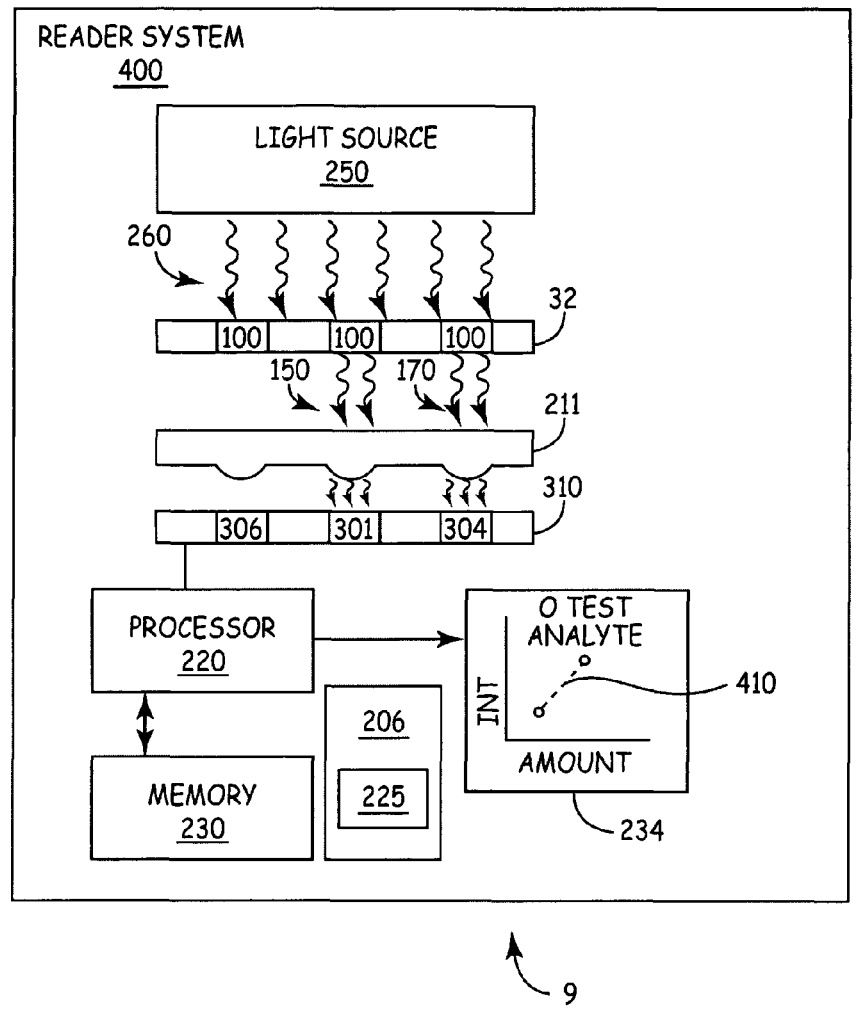
Figure 12B:
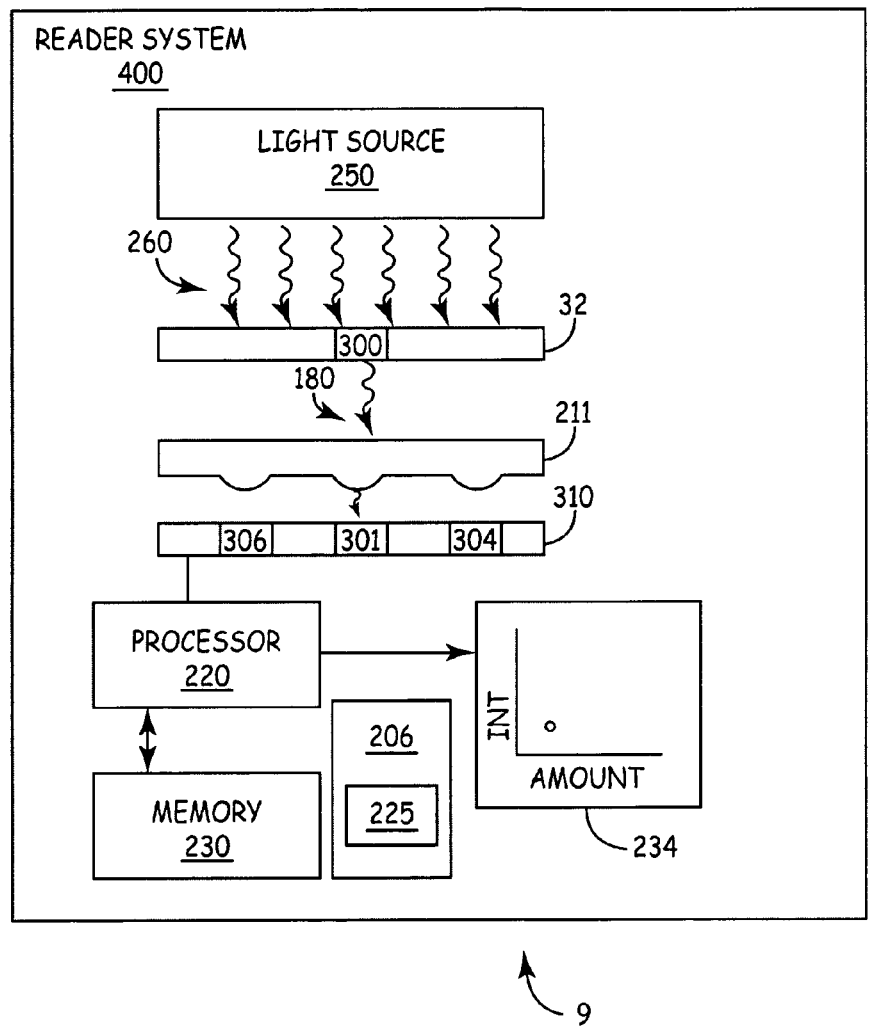
Figure 12C:
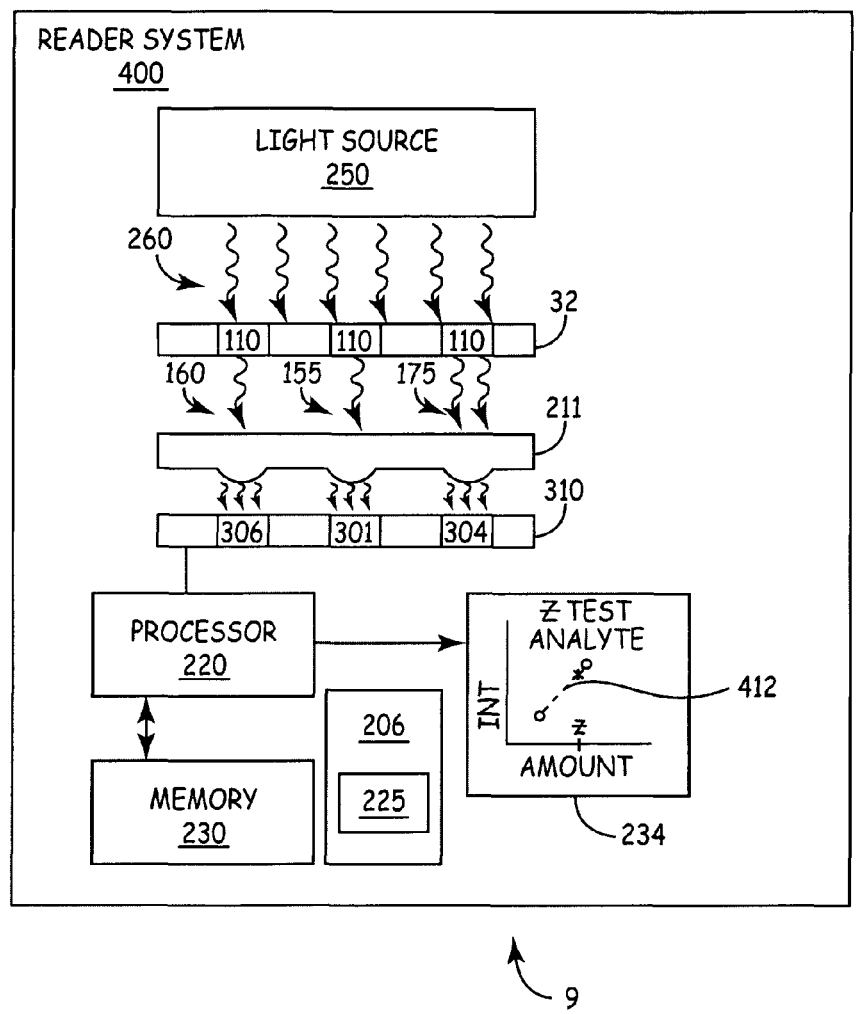

FIGS. 12A-12C are cross-sectional front views of one embodiment of a system to calibrate measurements of one or more test analytes from a test sample at different times during a calibration process.

In accordance with common practice, the various described features are not drawn to scale but are drawn to emphasize features relevant to the present invention. Reference characters denote like elements throughout figures and text.

DETAILED DESCRIPTION

In the following detailed description, reference is made to the accompanying drawings that form a part hereof, and in which is shown by way of illustration specific illustrative embodiments in which the invention may be practiced. These embodiments are described in sufficient detail to enable those skilled in the art to practice the invention, and it is to be understood that other embodiments may be utilized and that logical, mechanical and electrical changes may be made without departing from the scope of the present invention. The following detailed description is, therefore, not to be taken in a limiting sense.

Figure 1:
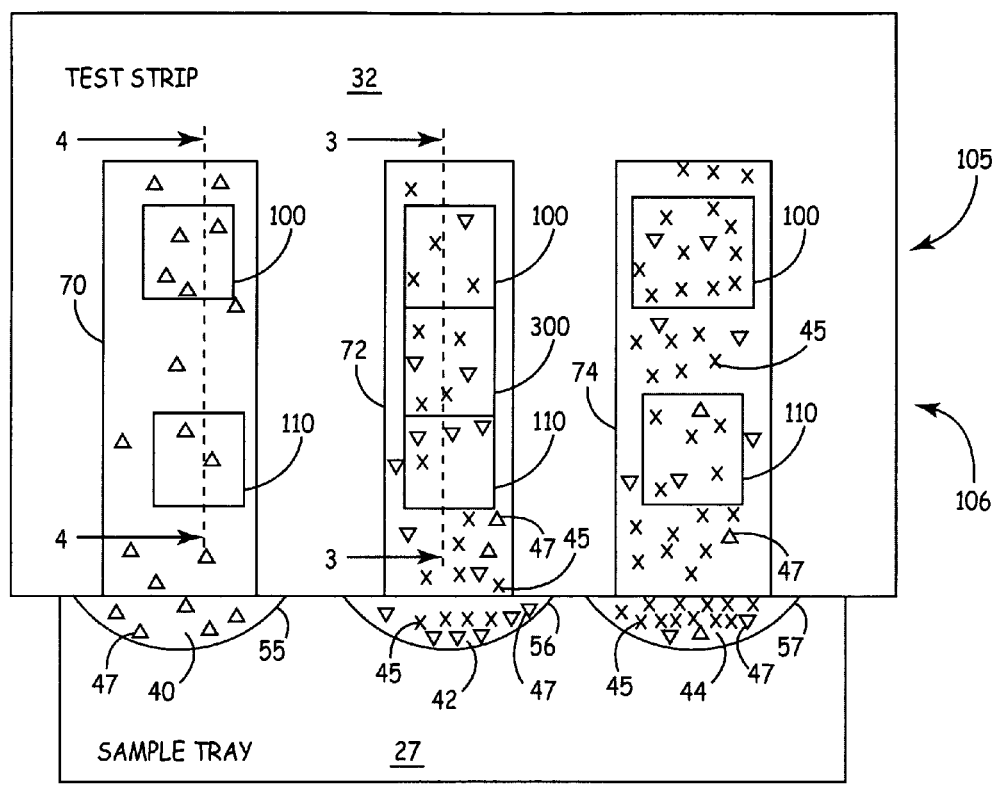
FIG. 1 is a block diagram of one embodiment of a test strip.

FIG. 1 is a block diagram of one embodiment of a test strip 32. The test strip 32 is used to calibrate measurements of one or more test analytes in a test sample 40. The test strip 32 is used in conjunction with a calibration system 10 or 11 as described below with reference to FIGS. 2 and 5. The test sample 40 is delivered from a well 55 of the sample tray 27 to a first channel 70 of the test strip 32. The test sample 40 includes a test analyte shown as a triangle and represented generally by 47. The test analyte 47 is also referred to here as "first test analyte 47." In one implementation of this embodiment, the test sample 40 is introduced to the first channel 70 through a hole in the test strip 32 that is located over the test-sample channel 70. In an implementation of this case, the test sample 40 is pipetted into the hole.

The test strip 32 comprises three channels: the first channel 70, a second channel 72, and a third channel 74. Each of the first channel 70, the second channel 72, and the third channel 74 comprise reagent portions 100 and reagent portions 110. The reagent portion 100 includes one type of reagent group and the reagent portion 110 includes another type of reagent group. The terms "reagent group" and "reagent" are used interchangeable throughout this document. As shown in FIG. 1, the row 105 is a row of reagent portions 100 and the row 106 is a row of reagent portions 110.

A test analyte 47 is reactive to a reagent if the test analyte 47 and the reagent attach or bond to each other when they contact each other. Such a bonding between the test analyte 47 and the reagent is referred to here as a bonding event. The contact required to initiate a bonding event occurs when the test analyte 47 flows through the first channel 70 past or through the reagent portion 100 and/or reagent portion 110.

If the test analyte 47 and the reagent group attach or bond to each other, the test analyte 47 is a reactive test analyte 47 to the respective reagent group.

In the embodiment of test strip 32, the second channel 72 includes a blank portion 300. The blank portion 300 does not include any reagent groups and is positioned between the reagent portion 100 and the reagent portion 110 within the second channel 72.

Figure 2:
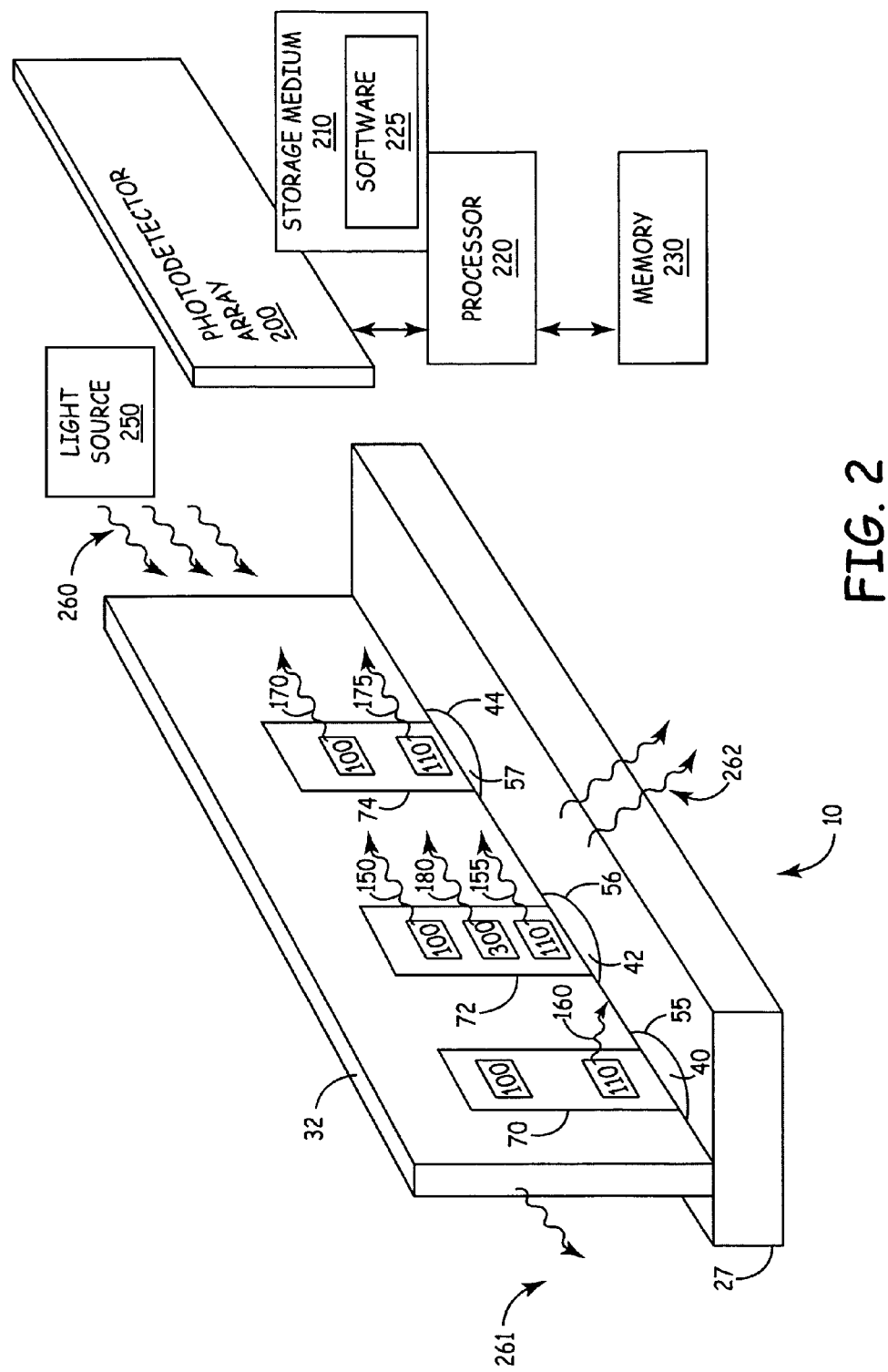
FIG. 2 is a block diagram of one embodiment of a system to calibrate measurements of one or more test analytes from a test sample.

FIG. 2 is a block diagram of a system 10 to calibrate measurements of one or more test analytes 47 (FIG. 1) from a test sample 40. The description of FIG. 2 is based on the test strip 32 described with reference to FIG. 1 although the description is relevant to other implementations of test strips. The system 10 comprises a photodetector array 200, a processor 220, a memory 230, at least one light source 250. The system 10 operates on the test strip 32, which receives samples from the sample tray 27. The system 10 also includes software 225, which is executed by the processor 220 to perform the operations described in this document. The software 225 is stored or otherwise embodied in or on a storage medium 226. In one implementation of this embodiment, the system 10 includes a test strip such as test strip 32. In another implementation of this embodiment, the system 10 includes a test strip and a sample tray, such as the test strip 32 and the sample tray 27.

As shown in FIG. 1, the first channel 70, also referred to here as "test-sample channel 70," receives the test sample 40. The test sample 40 includes either an unknown amount of at least one test analyte 47 or an undetectable amount of the test analyte 47, which is shown flowing in the first channel 70 over the reagent portions 110 and 100. If an undetectable amount of test analyte 47 is in the test sample 40, photodetectors in the calibration system do not sense any illumination from a reagent portion 100 in the test-sample channel 70 responsive to a bonding of the test analyte 47 and the reagent group in the reagent portion 100 during the calibration process. The calibration process is described below with reference to method 1000 of FIG. 10.

A photodetector in a photodetector array or a group of pixels in a photodetector array are both referred to here as a photodetector element. In one implementation of this embodiment, the calibration system does not sense any illumination generated responsive to a bonding event at a from a reagent portion 100 in the test-sample channel 70, since the generated illumination from the bonding event is at or below the noise floor of the photodetector element. In another implementation of this embodiment, the photodetector element in the calibration system does not sense any illumination from a reagent portion 100 in the test-sample channel 70 because there is no test analyte in the test sample 40 and therefore no bonding event occurred.

The second channel 72, also referred to here as a "first control channel 72," receives a first control sample 42 that is delivered from a well 56 of the sample tray 27. The first control sample 42 comprises control analytes, which are shown in the second channel 72 flowing over the reagent portions 110 and 100 and over the blank portion 300. The control analyte, shown as an "X" and represented generally by 45, is a known amount of a test analyte 45 reactive to reagents in the respective reagent portion 100. The control analyte 45 is also known as "first control analyte 45" and the known amount of the reactive test analyte 45 is a first known amount of the reactive test analyte 45. The control analyte 47, which is shown as triangles in FIG. 1, is a known amount of the test analyte 47 reactive to reagents in the reagent portion 110. The control analyte 47 is also known as "second control analyte 47" and the known amount of the reactive test analyte 47 is a first known amount of the reactive test analyte 47. Bonding events occur for the first control analyte 45 and the reagents in reagent portion 100 in the first control channel 72. Bonding events occur for the second control analyte 47 and the reagents in reagent portion 110 in the first control channel 72.

The third channel 74, also referred to here as "second control channel 74," receives a second control sample 44 that is delivered from a well 57 of the sample tray 27, which is shown in the second control channel 74 flowing over the reagent portions 110 and 100. The second control sample 44 also comprises the first control analyte 45 and the second control analyte 47. The second control sample 44 has a second known amount of the first test analyte 47 and a second known amount of the second test analyte 45. The second known amount is different from the first known amount. Bonding events occur for the first control analyte 45 and the reagents in reagent portion 100 in the second control channel 74. Bonding events occur for the second control analyte 47 and the reagents in reagent portion 110 in the second control channel 74.

In one implementation of this embodiment, more than two control analytes are included in the first control sample 42 and the second control sample 44. In another implementation of this embodiment, only one control analyte of the first known amount is included in the first control sample 42 and only one control analyte of the second known amount is in the second control sample 44.

In yet another implementation of this embodiment, the test strip includes more than two control channels. In yet another implementation of this embodiment, the test strip includes only one control channel. In yet another implementation of this embodiment, the test strip includes a blank channel having no reagent groups. In yet another implementation of this embodiment, the test strip includes more than one channel with a blank portion 300. Other implementations of embodiments of test strips are described below with reference to FIGS. 7 and 9.

In yet another implementation of this embodiment, there is more than one reagent portion 100 in the first channel 70, the second channel 72, and the third channel 74. In yet another implementation of this embodiment, there is more than one reagent portion 100 and more than one reagent portion 110 in the first channel 70, the second channel 72, and the third channel 74.

The test sample 40 can be a patient sample, a forensic sample, a biological sample or a chemical sample. The test sample 40, the first control sample 42 and the second control sample 44 are fluid samples having a viscosity to permit wicking in the respective test-sample channel 70, first control channel 72 and third control channel 74. In one implementation of this embodiment, the control samples 42 and 44 include a base fluid to which the known amounts of one or more control analytes are added.

The test sample 40 is wicked into the test-sample channel 70 by capillary action. The first control sample 42 and the second control sample 44 are wicked into the first control channel 72 and the second control channel 74, respectively, by capillary action. The first channel 70, the second channel 72 and the third channel 74 can be gel channels, capillary channels, glass channels, paper channels, wettable-fiber channels. One or more of the first channel 70, the second channel 72 and the third channel 74 can be a different type of channel than the other channels. In one implementation of this embodiment, the reagent portion 100 and the reagent portion 110 are inside the capillary channels. In another implementation of this embodiment, the reagent portion 100 and the reagent portion 110 are embedded in the material that forms the capillary channels. In yet another implementation of this embodiment, the reagent portion 100 and the reagent portion 110 overlay the material that forms the capillary channels so that the sample material touches the reagent portions 100 and the reagent portions 110 when the sample is wicked through the channels.

As shown in FIG. 1, the test sample 40 and the control samples 42 and 44 are delivered to the test strip 32 by a sample tray 27. Other methods of delivery of the test sample 40 and the control samples 42 and 44 can be used to allow the test sample 40 and the control samples 42 and 44 to wick into the respective channels. In one implementation of this embodiment, the wells 55, 56 and 57 are not on a single tray or substrate. In another implementation of this embodiment, hypodermic needles deliver the test sample 40 and the control samples 42 and 44 to the respective first channel 70, the second channel 72 and the third channel 74.

The light source 250 illuminates the test strip 32 with light 260. A portion of the light 260 that is incident on the test strip 32 is reflected as light 262. A portion of the light 260 that is incident on the test strip 32 is transmitted through the test strip 32 as light 261. A portion of the light 260 interacts with the reagent portion 100. The processor 220 is communicatively coupled to the photodetector array 200 and the memory 230. In one implementation of this embodiment, the memory 230 is integral to the photodetector array 200. The system 10 calibrates measurements of one or more test analytes 47 in a test sample 40 while the photodetector array 200, the light source 250 and the test strip 32, have relative positions in pre-selected locations. The relative positions include specific distances between the photodetector array 200, the light source 250 and the test strip 32. The relative positions also include specific angles between the surfaces of the photodetector array 200, the light source 250 and the test strip 32.

In one implementation of this embodiment, a portion of the light 260 incident on the test strip 32 is transmitted through the test strip 32 as light 261 and none of the light 260 is reflected from the test strip 32. In another implementation of this embodiment, a portion of the light 260 is reflected as light 262 and none of the light 260 is transmitted through the test strip 32. In yet another implementation of this embodiment, at least a portion of the light 260 is absorbed by the test strip 32.

If a bonding event has occurred at one or more of the reagent portions 100 and 110 on the test strip 32, the light 260 stimulates the emission of a reaction light having a reaction light level from the reagent portion 100 and 110 in which the bonding event occurred. In one implementation of this embodiment, if a bonding event has occurred at one or more of the reagent portions 100 and 110 on the test strip 32, the light 260 is reflected as reaction light having a reaction light level from the reagent portion 100 and 110 in which the bonding event occurred. The bonding events and the generation of reaction light in the test strip 32 is described now with reference to FIGS. 3A, 3B, 4A and 4B.

Figure 3A:
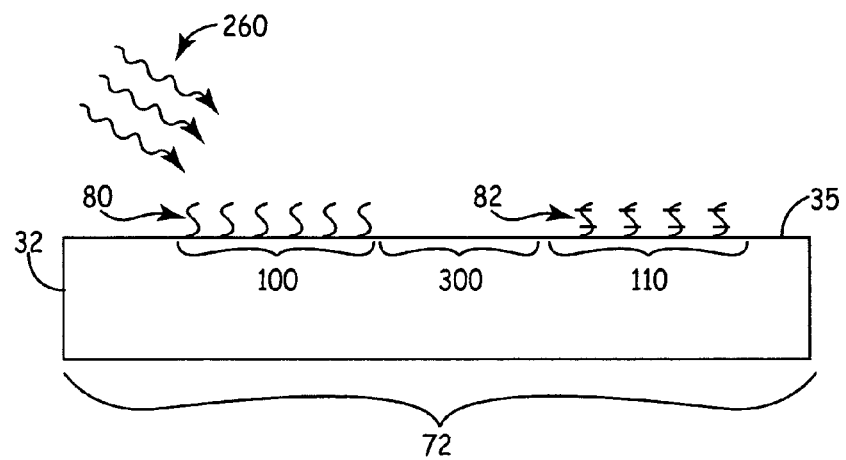
FIGS. 3A and 3B are side cross-sectional views of one embodiment of the control channel during a calibration process before and after a bonding event, respectively.
Figure 3B:
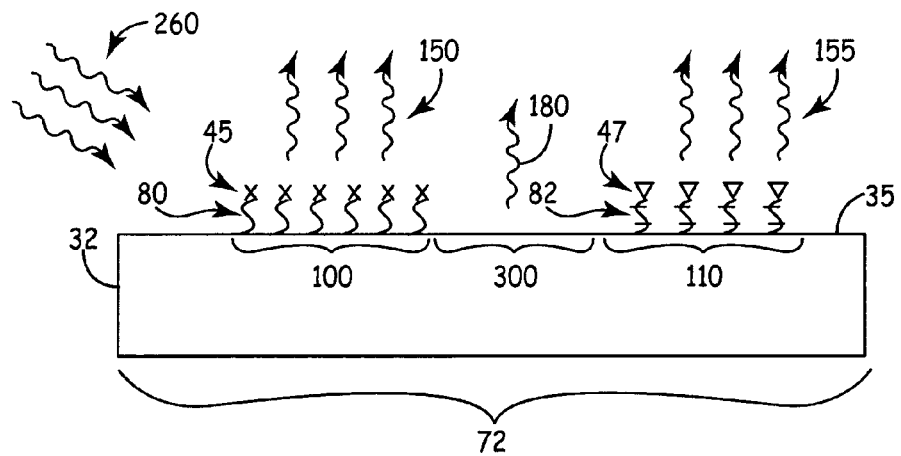

FIGS. 3A and 3B are side cross-sectional views of one embodiment of the control channel 72 during a calibration process before and after a bonding event, respectively. The plane upon which the cross-section views of FIGS. 3A and 3B are taken is indicated by section line 3-3 in FIG. 1. The reagent group represented generally by 80 in the reagent portion 100 is attached to a surface 35 of the test strip 32 in first control channel 72. The reagent group 80 is also referred to here as "first reagent group 80." The reagent group represented generally by 82 in the reagent portion 110 is attached to the surface 35 of the test strip 32 in first control channel 72. The reagent group 82 is also referred to here as "second reagent group 82." The reagent portion 100 is spatially separated from the reagent portion 110 by the blank portion 300. There is no reagent group attached to the surface 35 of the test strip in the blank portion 300. As shown in FIG. 3A, light represented generally by 260 is incident on the surface 35 of the test strip 32 before a bonding event and no reaction light is emitted from the reagent portion 100 or the reagent portion 110. Any light 260 reflected from the surface 35 is not shown.

As shown in FIG. 3B, light 260 is incident on the surface 35 of the test strip 32 after a bonding event so reaction light represented generally by 150 is emitted from the reagent portion 100 of the first control channel 72 and reaction light represented generally by 155 is emitted from the reagent portion 110 of the first control channel 72. The control analyte represented generally by 45, which is a first known amount of a test analyte 45 that may or may not be in the test sample 40, is bonded to the first reagent group 80.

When subjected to the light 260, the control analyte 45 bonded to the reagent group 80 is stimulated to emit reaction light 150. In one implementation of this embodiment, light 260 is reflected from the control analyte 45 bonded to the reagent group 80. A photodetector element of the photodetector array 200 detects the reaction light 150 and the processor 220 that is communicatively coupled to the photodetector array 200 determines a first reaction light level correlated to the reaction light 150 detected from the reagent portion 100 in the first control channel 72.

Based on the location of the photodetector element of the photodetector array 200 that detects the reaction light 150, the processor 220 is able to determine that the reaction light 150 originated at the reagent portion 100 in the first control channel 72. The determination is made because the system 10 calibrates measurements of one or more test analytes 47 in a test sample 40 when the photodetector array 200, the light source 250 and the test strip 32 have relative positions in pre-selected locations. Based on the pre-selected relative positions and the angle subtended by the emitted light, the light emitted from known locations on the test strip 32 is correlated to known locations on the photodetector array 220. These correlated positions are stored in the memory 230, which is communicatively coupled to the processor 220. The processor 220 retrieves the information as needed from memory 230 to determine that the reaction light 150 originated at the reagent portion 100 in the first control channel 72.

Likewise, when subjected to the light 260, the control analyte 47 bonded to the reagent group 82 is stimulated to emit reaction light 155. In one implementation of this embodiment, light 260 is reflected from the control analyte 47 bonded to the reagent group 82. A photodetector element of the photodetector array 200 detects the reaction light 155 and the processor 220 determines a first reaction light level correlated to the reaction light 155 detected from the reagent portion 110 in the second control channel 74.

Based on the location of the photodetector element of the photodetector array 200 that detects the reaction light 155, the processor 220 is able to determine that reaction light 155 originated at the reagent portion 110 in the first control channel 72 using the correlated positions stored in the memory 230.

When subjected to the light 260, the blank portion 300 reflects a portion of the light 260 as reference light represented generally by 180 into the photodetector array 200. Reference light 180 also includes ambient light (not shown) that reflects from the surface 35. There can be other sources of reference light 180. The photodetector array 200 detects the reference light 180 and the processor 220 determines a reference-light level correlated to the reference light 180 detected from the blank portion 300 in the first control channel 72. Based on the location of the photodetector element of the photodetector array 200 that detects the light, the processor 220 is able to determine by that the reference light 180 originated at the blank portion 300 in the first control channel 72 using the correlated positions stored in the memory 230.

Figure 4A:
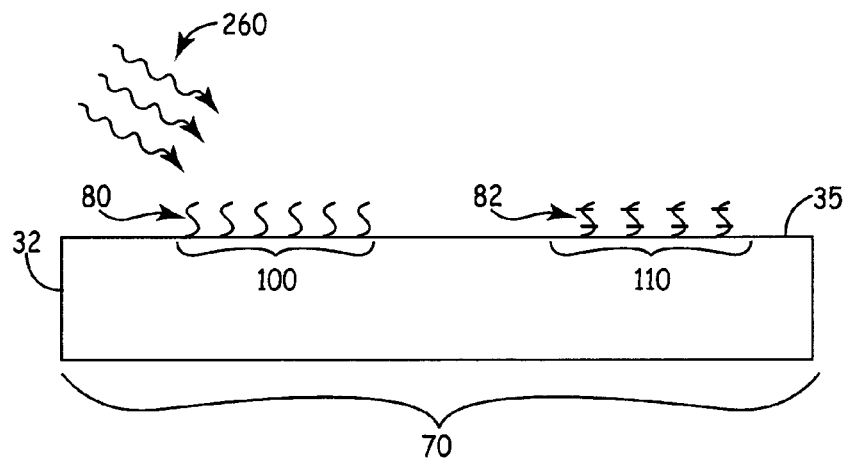
FIGS. 4A and 4B are side cross-sectional views of one embodiment of a test-sample channel during a calibration process before and after a bonding event, respectively.
Figure 4B:
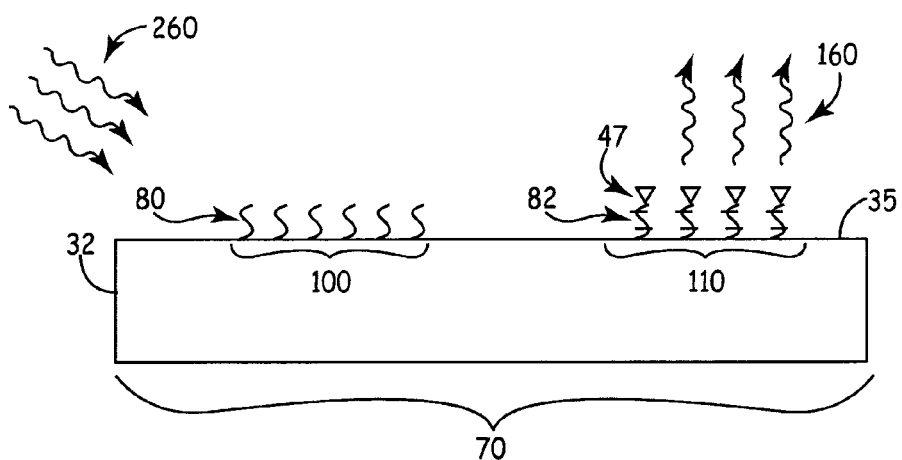

FIGS. 4A and 4B are side cross-sectional views of one embodiment of a test-sample channel 70 during a calibration process before and after a bonding event, respectively. The plane upon which the cross-section view of FIGS. 4A and 4B are taken is indicated by section line 4-4 in FIG. 1. The reagent group 80 in the reagent portion 100 is attached to the surface 35 of the test strip 32 in the test-sample channel 70. The reagent group 82 in the reagent portion 110 is attached to a surface 35 of the test strip 32 in the test-sample channel 70. The reagent portion 110 is spatially separated from the reagent portion 110 by a region in which there is no reagent group attached to the surface 35 of the test strip 32. In one implementation of this embodiment, the reagent portion 100 is adjacent to the reagent portion 110. As shown in FIG. 4A, light 260 is incident on the surface 35 of the test strip 32 before a bonding event so no reaction light is emitted from the reagent portion 100 or the reagent portion 110. Any light 260 reflected from the surface 35 is not shown.

As shown in FIG. 4B, light 260 is incident on the surface 35 of the test strip 32 after a bonding event, so test light represented generally by 160 is emitted from the reagent portion 110 of the test-sample channel 70.

The test analyte 47, from the test sample 40 having an unknown amount of a test analyte 45, is bonded to the reagent group 82. When subjected to the light 260, the test analyte 47 bonded to the reagent group 82 is stimulated to emit test light 160. A photodetector element of the photodetector array 200 detects the test light 160 and the processor 220 determines a test-light level correlated to the test light 160 emitted from the reagent portion 110 in the test-sample channel 70. The processor 220 is able to determine by the location of the photodetector element of the photodetector array 200 that detects the test light 160, that the test light 160 originated at the reagent portion 110 in the test-sample channel 70.

However, since the exemplary test sample 40 (as shown in FIG. 1) does not include any test analyte 45, there is no bonding of test analytes to the reagent portion 100 in the test-sample channel 70. When test-sample channel 70 is subjected to the light 260, the reagent group 80 is not stimulated to emit (or reflect) any light. A photodetector element of the photodetector array 200 detects only ambient light but no light due to a bonding event at the reagent portion 100 in the test-sample channel 70. The processor 220 is able to determine by the location of the photodetector element of the photodetector array 200 that detects the ambient light (or light 260 reflected from the reagent portion 100). Based on the determined position, the processor 220 is able to determine that only ambient light (or light 260 reflected from the reagent portion 100) originated at the reagent portion 100 in the test-sample channel 70.

The photodetector array 200 detects light correlated to at least two reagent portions 100 and 110 of the test strip 32. The photodetector array 200 detects a reference light from at least one blank portion 300 of the test strip 32.

The photodetector array 200 is a photodetector, a one-dimensional photodetector array, a two-dimensional photodetector array, a charge-coupled device camera, an array of complimentary metal-oxide-semiconductor image sensors, or combinations thereof.

Figure 5:
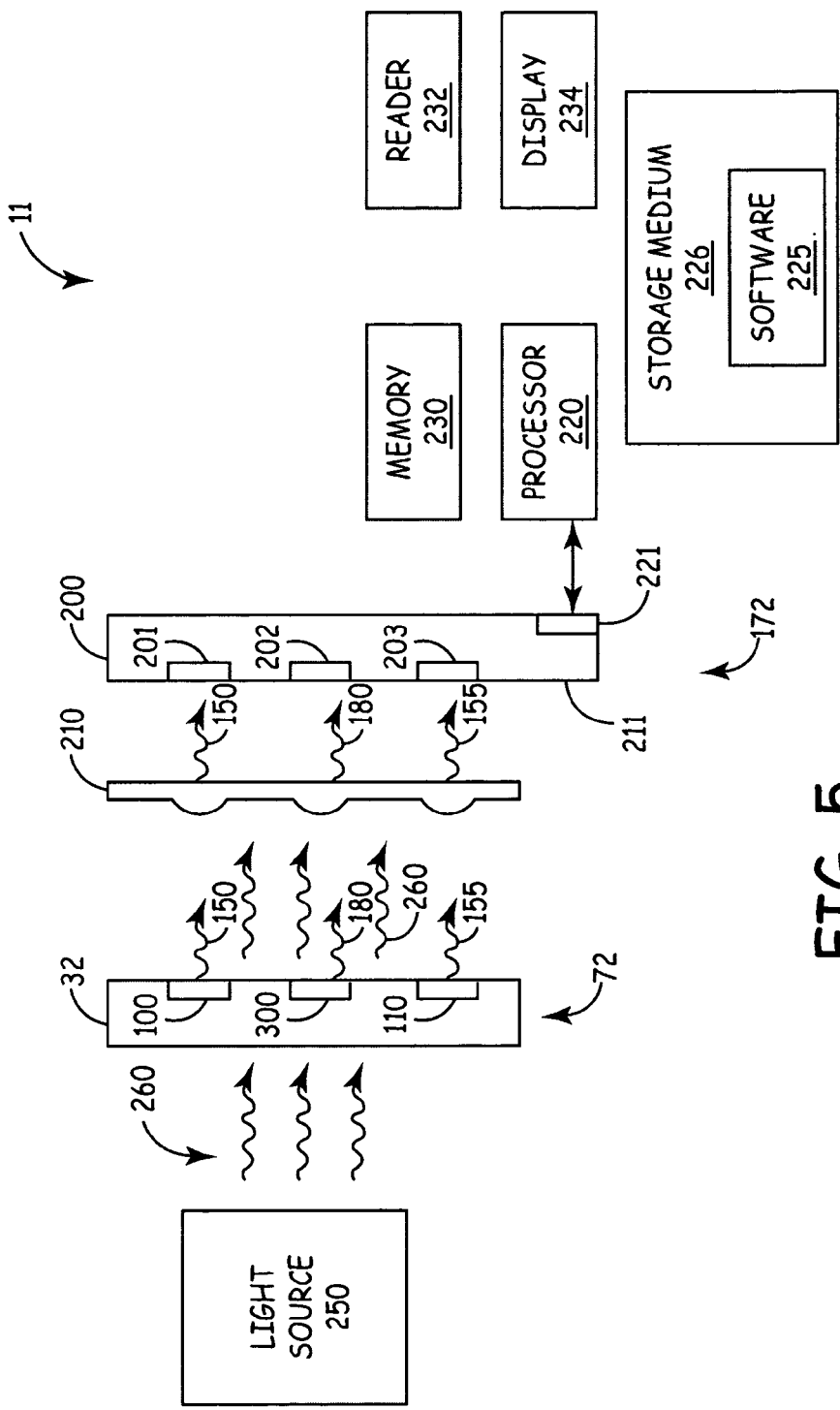
FIG. 5 is a block diagram of one embodiment of a system to calibrate measurements of one or more test analytes from a test sample.

FIG. 5 is a block diagram of one embodiment of a system 11 to calibrate measurements of one or more test analytes 45 from a test sample 40. The system 10 differs from the system 10 of FIG. 2, in that a lens system 210 is included in system 10 and a processor 221 is included in the photodetector array 200. The system 11 also includes a display 234 and a reader 232 which are used to display calibration curves or display in text format the amount of one or more test analytes 45. In one implementation of this embodiment, the system 11 includes a test strip such as test strip 32. In another implementation of this embodiment, the system 11 includes a test strip and a sample tray, such as test strip 32 and the sample tray 27. In one implementation of this embodiment, all the described functions of processor 220 are performed by the processor 221 in the photodetector array 200. In another implementation of this embodiment, the described functions of processor 220 are shared by the processor 220 and the processor 221 in the photodetector array 200.

In FIG. 5, the test strip 32, the lens system 210 and the photodetector array 200 are shown in a side cross-sectional view. The side cross-sectional view of the test strip 32 is similar to the side cross-sectional view of FIG. 3B. In FIG. 5, the reagent groups 80 and 82 are not shown. The photodetector array 200 and the operation of system 11 are discussed with reference to FIG. 5 and FIG. 6.

Figure 6:
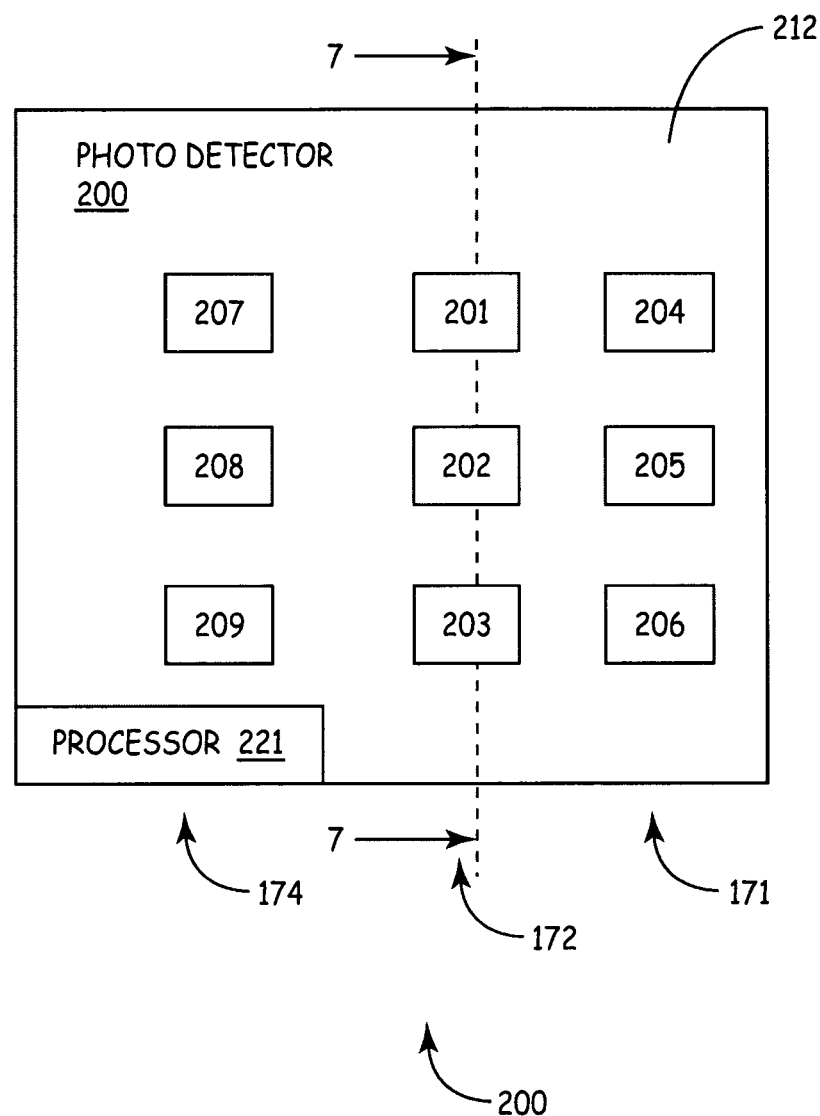
FIG. 6 is a block diagram of one embodiment of a photodetector array.

FIG. 6 is a block diagram of one embodiment of a photodetector array 200. The photodetector elements 201, 202 and 203 on or at the surface 212 of the photodetector array 200 as shown in the side cross-sectional view of FIG. 5. The photodetector elements 201-209 of the photodetector array 200 are shown arranged on the surface 212 in a rectangular array.

The column 174 of the photodetector array 200 includes photodetector elements 207, 208 and 209. Test light from the reagent portion 100 (FIG. 2) in the test-sample channel 70 is focused by the lens system 210 onto the photodetector element 207. Test light from the reagent portion 110 (FIG. 2) in the test-sample channel 70 is focused by the lens system 210 onto the photodetector element 209. In one implementation of this embodiment, the photodetector element 208 is not in the photodetector array 200.

The column 172 of the photodetector array 200 includes photodetector elements 201, 202 and 203. Reaction light 150 from the reagent portion 100 in the second channel 72 is focused by the lens system 210 onto the photodetector element 201. Reference light 180 from the blank portion 300 in the second channel 72 is focused by the lens system 210 onto the photodetector element 202. Reaction light 155 from the reagent portion 100 in the second channel 72 is focused by the lens system 210 onto the photodetector element 203. As shown in FIG. 5, a portion of the light 260 from the light source 250 is transmitted through the test strip 32. Light 260 incident on the photodetector array 200 is detected at the photodetector element 208 (FIG. 6) and the light intensity is normalized for the intensity of the light transmitted through the blank portion 300 of the test strip 32.

The column 171 of the photodetector array 200 includes photodetector elements 204, 205 and 206. Reaction light represented generally by 170 from the reagent portion 100 (FIG. 2) in the third channel 74 is focused by the lens system 210 onto the photodetector element 204. Reaction light represented generally by 175 from the reagent portion 110 (FIG. 2) in the third channel 74 is focused by the lens system 210 onto the photodetector element 206. In one implementation of this embodiment, the photodetector element 205 is not in the photodetector array 200.

These correlated positions, such as the correlation between reagent portion 100 and the photodetector element 201 shown in FIG. 5, are stored in the memory 230, which is communicatively coupled to the processor 220. The processor 220 retrieves the information as needed from memory 230 to determine that the reaction light 150 originated at the reagent portion 100 in the first control channel 72.

In one implementation of this embodiment, the photodetector elements 201-209 are single photodetectors positioned in an array on the surface 212. In another implementation of this embodiment, the photodetector elements 201-209 are each a group of pixels in a photodetector array 220. In yet another implementation of this embodiment, the photodetector elements 201-209 are each a pixel in a photodetector array 220.

In yet another implementation of this embodiment, each sensor element is a complementary metal-oxide-semiconductor (CMOS) sensor element. Each sensor element may alternatively be a charge-coupled device (CCD) sensor element or another suitable type of sensor element that generates an electrical signal in response to incident light. In one implementation of this embodiment, the lens system 210 is an array of diffractive optical elements etched or molded in a plastic substrate. In another implementation of this embodiment, the lens system 210 is an array of lenses positioned in securing framework. There are other ways to form the lens system 210. The lenses in the lens system 210 are designed based on the specific distances between the photodetector array 200, the light source 250 and the test strip 32, the wavelengths of the light being focused and the specific angles between the surfaces of the photodetector array 200, the light source 250 and the test strip 32. In another implementation of this embodiment, the lens system 210 is coated with a coating to prevent the transmission of the wavelength or wavelengths of the light 260.

Figure 7:
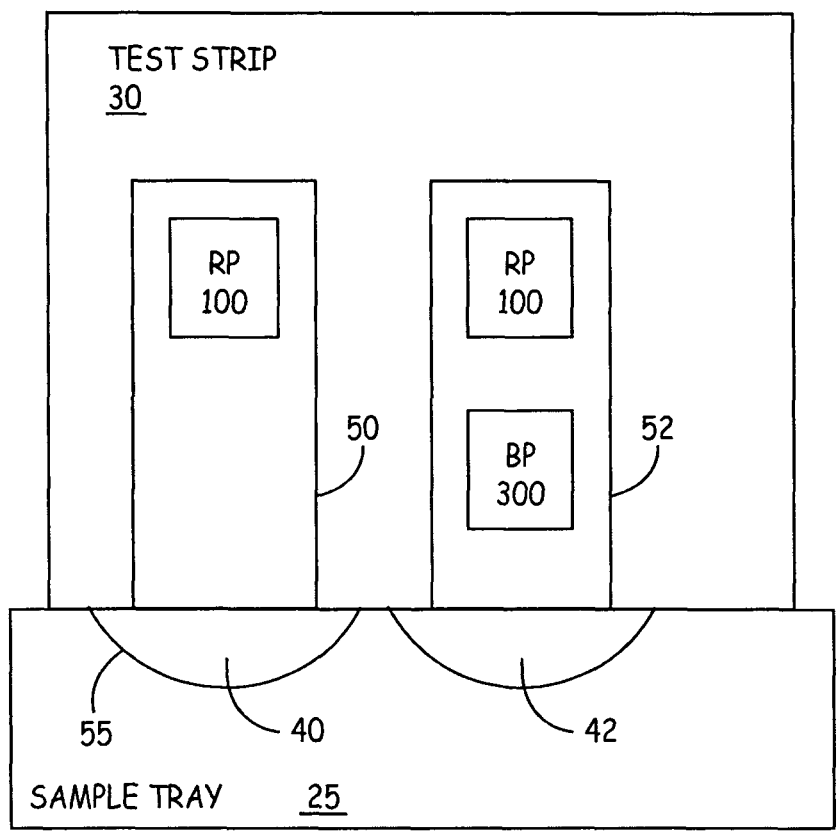
FIG. 7 is a block diagram of one embodiment of a test strip.

FIG. 7 is a block diagram of one embodiment of a test strip 30. Test strip 30 is used to calibrate measurements of one analyte in a test sample 40. The test strip 32 can be used in conjunction with a calibration system 10 or 11 as described above below with reference to FIGS. 2 and 5, respectively. The test sample 40 is delivered from a well 55 of the sample tray 25 to a first channel 70 of the test strip 30. The test sample 40 includes a test analyte as described above with reference to FIGS. 1 and 2.

The test strip 30 comprises two channels: the first channel 50, a second channel 52. Each of the first channel 50 and the second channel 52 comprise a reagent portion 100. The reagent portion 100 includes one type of reagent group. In the embodiment of test strip 30, the second channel 52 includes a blank portion 300. The blank portion 300 does not include any reagent groups.

Figure 8:
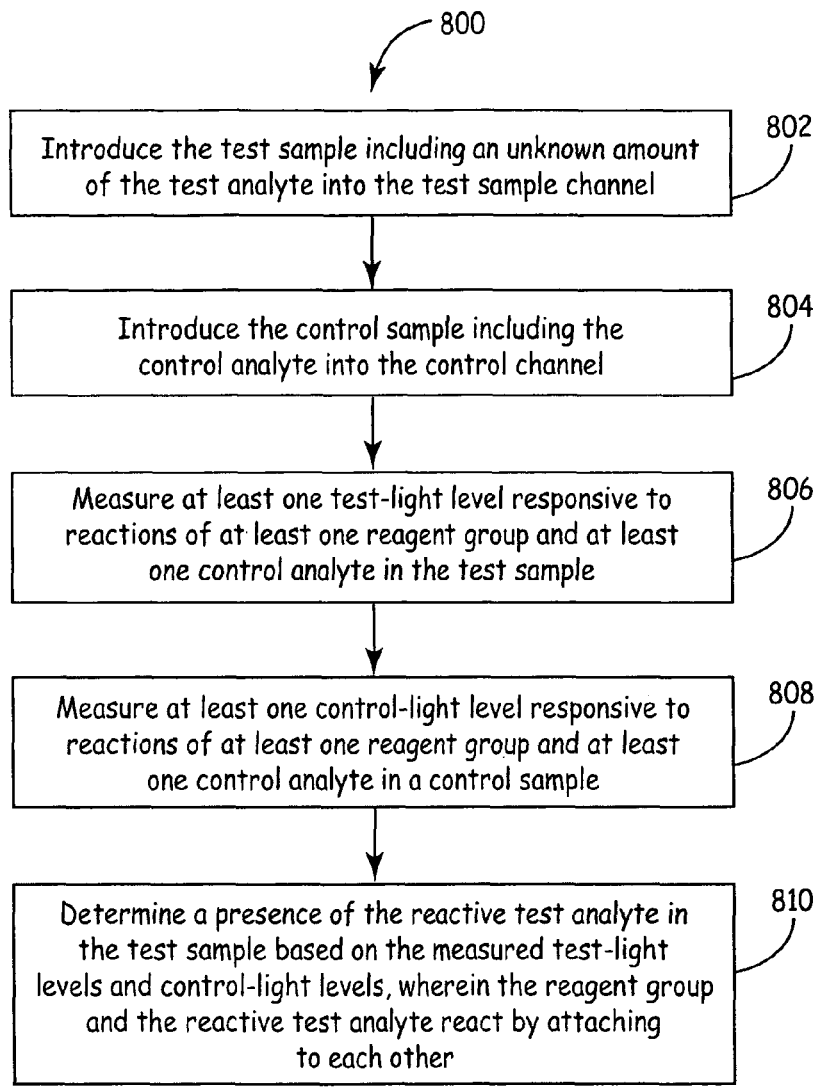
FIG. 8 is a flow diagram of one embodiment of a method to determine a presence of a reactive test analyte in a test sample.

FIG. 8 is a flow diagram of one embodiment of a method 800 to determine a presence of a reactive test analyte 45 in a test sample 40. The particular embodiment of method 800 shown in FIG. 8 is described here as being implemented using the test strip 30 in the system 11 described above with reference to FIG. 5. Specifically method 800 is implemented using the test-sample channel 70 and one control channel 72. In one implementation of this embodiment, the software 225 is executed by the processor 220 to perform the operations described with reference to method 800. In another implementation of this embodiment, the software 225 is executed by the processor 221 in the photodetector array 200 to perform the operations described with reference to method 800.

At block 802, a test sample 40 including an unknown amount of the test analyte 45 is introduced into the test-sample channel 70. The test sample 40 is wicked into the test-sample channel 70 from the well 55 of the sample tray 27. At block 804, the control sample 42 including at least one control analyte 45 and/or control analyte 47 into the control channel 72. The control sample 42 is wicked into the control channel 72 from the well 56 of the sample tray 27.

At block 806, processor 220 measures at least one test-light level responsive to reactions of at least one reagent group 80 and/or reagent group 82 (FIG. 4B) and at least one reactive test analyte 47 (FIG. 4B) in the test sample 40. The test light 160 is incident on a photodetector element 209 (FIG. 6) in the photodetector array 200. The photodetector element 209 generates a signal responsive to the incident test light 160. The signal is input to processor 220. The processor 220 generates a test-light level that is correlated to the signal received from the photodetector element 209. In this manner the processor 220 measures a test-light level responsive to reactions of at least one reagent group 82 (FIG. 4B) and at least one reactive test analyte 47 (FIG. 4B) in the test sample 40.

At block 808, processor 220 measures at least one control-light level responsive to reactions of at least one reagent group 80 and/or reagent group 82 (FIG. 4B) and at least one control analyte 47 and/or 47 (FIG. 3B) in the control sample 42. Each control analyte is a known amount of at least one reactive test analyte as described above with reference to FIGS. 2, 3A, 3B, 4A and 4B.

The reaction light 150 is incident on the photodetector element 201 (FIG. 5) in the photodetector array 200. The photodetector element 201 generates a signal responsive to the reaction light 150. The signal is input to processor 220. The processor 220 generates a control-light level that is correlated to the signal received from the photodetector element 201. In one implementation of this embodiment, the reference-light level is measured by the processor 220 in a manner similar to the manner in which the control-light level is measured.

At block 810, the processor 220 determines a presence of the reactive test analyte 47 in the test sample 40 based on the measured test-light levels and control-light levels. If the test-light level is below the control-light level, then the amount of the test analyte is less than the amount of test analyte in the control sample. If the test-light level is above the control-light level, then the amount of the test analyte is greater than the amount of test analyte in the control sample. If the test-light level is above the reference-light level, then the test analyte is present in the test sample. Likewise, if the test-light level is at or below the reference-light level, then the test analyte is not present in the test sample.

The wavelength of the lights 260, 150, 155, 180, 160, 170 and 175 described here are dependent upon the reagent groups and the analytes. For all the implementations described herein, the wavelength of the light 260 is suited to cause an attached reagent group and the reactive test analyte to emit light of a known wavelength. In one implementation of this embodiment, the light source 250 emits light 260 having more than one wavelength from different spectral regions. In another implementation of this embodiment, the light source 250 emits light 260 having wavelengths over a continuous range of wavelengths.

The photodetector elements 201-209 are suited to detect the wavelengths of the emitted test light 160 and control light 150, 155, 170 and 175 and reference light 180. In one implementation of this embodiment, the photodetector elements 201-209 detect different ranges of wavelengths. The systems 10 and 11 are designed for various test analytes reacting with specific reagents that emit light or reflect light of a known wavelength based on the wavelength of the light 260 emitted from the light source 250.

Figure 9:
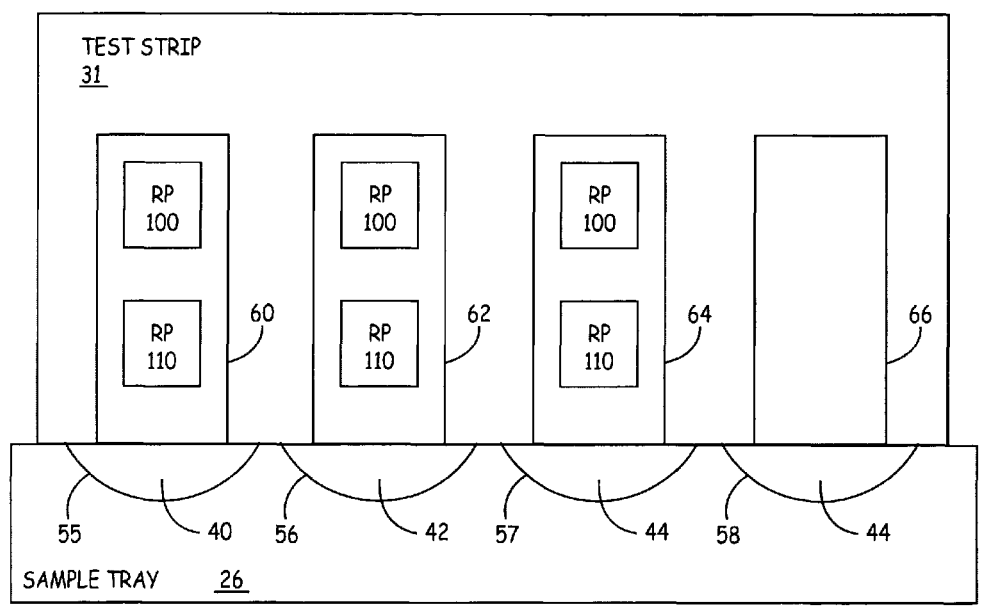
FIG. 9 is a block diagram of one embodiment of a test strip.

FIG. 9 is a block diagram of one embodiment of a test strip 31. The test strip 31 is used to calibrate measurements of one or more test analytes in a test sample 40. The test strip 31 is used in conjunction with a calibration system 10 or 11 as described below with reference to FIGS. 2 and 5, respectively.

The test strip 31 comprises four channels: the first channel 60, a second channel 62, a third channel 64 and a fourth channel 66. Each of the first channel 60, the second channel 62, and the third channel 64 comprise reagent portions 100 and reagent portions 110. The fourth channel 66 does not include any reagent portions and as such is equivalent to the blank portion 300 in the test strip 32.

The first channel 60, also referred to here as "test-sample channel 60," receives the test sample 40 as described above with reference to FIG. 1. The second channel 62, also referred to here as a "first control channel 62," receives a first control sample 42 that is delivered from a well 56 of the sample tray 26. The third channel 64, also referred to here as "second control channel 64," receives a second control sample 44 that is delivered from a well 57 of the sample tray 26. The fourth channel 66, also referred to here as "blank channel 66," receives the second control sample 44 that is delivered from a well 58 of the sample tray 26.

Figure 10:
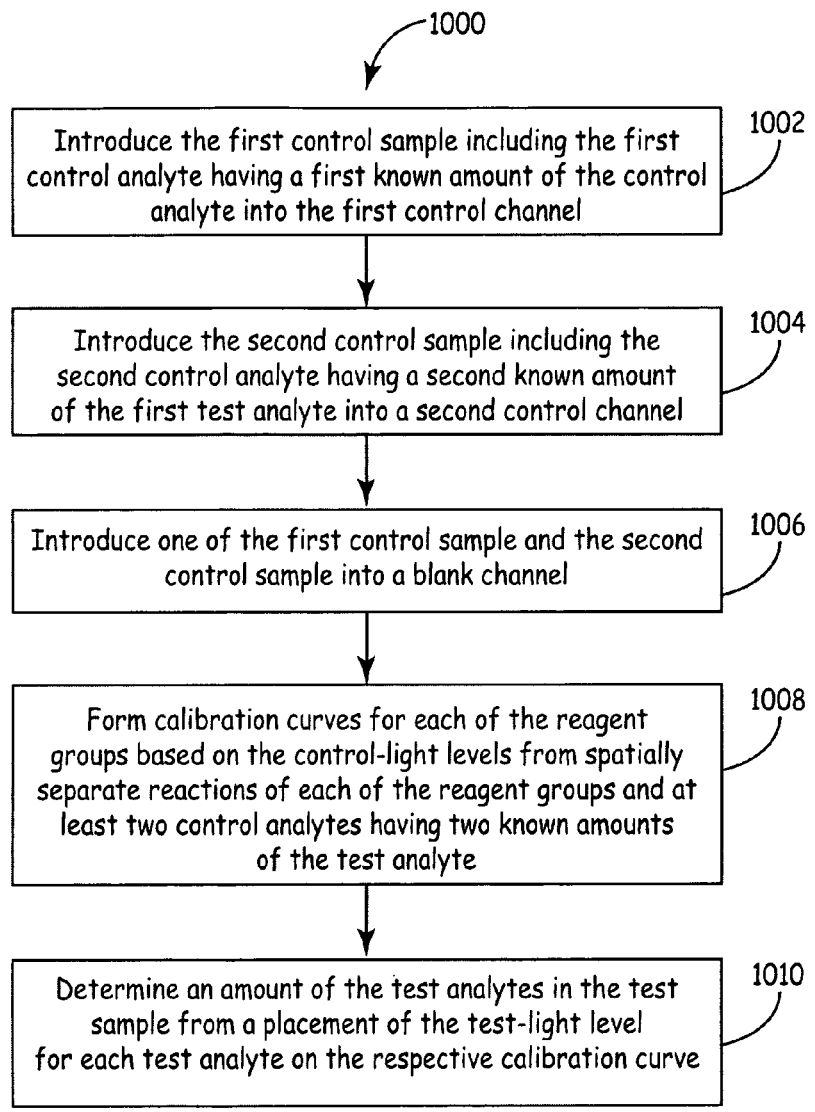
FIG. 10 is a flow diagram of one embodiment of a method to determine an amount of a reactive test analyte in a test sample.

FIG. 10 is a flow diagram of one embodiment of a method 1000 to determine an amount of a reactive test analyte 45 in a test sample 40. The particular embodiment of method 1000 shown in FIG. 10 is described here as being implemented using either system 10 or 11 described above with reference to FIGS. 2 and 5, respectively, operating on the test strip 31 described above with reference to FIG. 9. The exemplary test strip 31 is similar to the exemplary test strip 32 in that the reagent portions 100 and 110 react to control analytes 45 and 47, respectively. The blank portion 300 of test strip 32 is equivalent to the blank channel 66 of test strip 31.

Method 1000 is implemented for a system having at least two control channels. The software 225 is executed by the processor 220 to perform the operations described with reference to method 1000.

Method 1000 is implemented with portions of method 800. Method 1000 begins after block 802 of method 800 is implemented for the test strip 31, so that the test sample 40 including an unknown amount of the test analyte 45 has been introduced into the test-sample channel 60 from the well 55 of the sample tray 26 prior to step 1002. In one implementation of this embodiment, the process at blocks 802 and 1002 occur at the same time.

At block 1002, the first control sample 42 including the first known amount of control analyte 47 is introduced into the first control channel 62. In one implementation of this embodiment, the first control sample 42 also includes a first known amount of control analyte 45 so both the control analyte 45 and 47 are introduced into the first control channel 62.

At block 1004, the second control sample 44 including the second control analyte 47 having a second known amount of the first test analyte 47 is introduced into the second control channel 64. In one implementation of this embodiment, the second control sample 44 also includes a second known amount of control analyte 45 so both the control analyte 45 and 47 are introduced into the second control channel 64.

At block 1006, the second control sample 44 including the second control analyte 47 having a second known amount of the first test analyte 47 is introduced into the blank channel 66. In one implementation of this embodiment, the first control sample 42 including the first control analyte 47 having a first known amount of the first test analyte 47 is introduced into the blank channel 66.

Before block 1008 is implemented, blocks 806 and 808 in the method 800 of FIG. 8 are implemented and the processor 220 determines reaction light levels correlated to the light detected from each of the reagent portions 100 and 110. The processor 220 also determines the reference-light levels correlated to the blank channel 66 (or blank portion 300 of test strip 32).

The processor 220 measures at least one first control-light level responsive to reactions of at least one first reagent group 80 and/or second reagent group 82 (FIG. 4B) and at least one control analyte 45 and/or 47 (FIG. 3B) in the control sample 42 after it flows through the first control channel 62. As described above, the first control light is emitted from the test strip 31 after light 260 is incident on the test strip 31 and the processor 220 determines a first reaction light level for the first control light.

The processor 220 also measures at least one second control-light level responsive to reactions of at least one first reagent group 80 and/or second reagent group 82 and at least one control analyte 45 and/or 47 in the control sample 44 after it flows through the second control channel 64. As described above, the second control light is emitted from the test strip 31 after light 260 is incident on the test strip 31 and the processor 220 determines the second reaction light level for the second control light.

The processor 220 also measures at least one test-light level responsive to reactions of at least one reagent group 80 and/or reagent group 82 and at least one reactive test analyte 45 and/or 47 in the test sample 40. As described above, the test light is emitted from the test strip 31 after light 260 is incident on the test strip 31 and the processor 220 determines a third reaction light level (also referred to here as test-light level) for the test light.

The processor 220 also determines at least one reference-light level responsive to at least one control analyte 45 and/or 47 in the control sample 44 flowing through the blank channel 66. The control sample 44 may have absorptive or reflective qualities that modify the control light emitted (or reflected) from the test strip 31. The reference light from the blank channel 66 (or from the blank portion 300) is dependent upon such absorptive or reflective qualities of the control sample. The reference light from the blank channel 66 is independent upon the qualities of the reaction between any analytes and reagents.

In one implementation of this embodiment, the processor 220 adjusts each reaction light level by the reference-light level. The processor 220 subtracts the reference-light level from the reaction light levels for each reagent group to form adjusted reaction light levels. The processor 220 subtracts the reference-light level from the test-light levels to form adjusted test-light levels. The processor 220 subtracts the reference-light level from the control-light levels to form adjusted control-light levels.

At block 1008, the processor 220 forms calibration curves for each of the reagent groups based on the control-light levels from spatially separate reactions of each of the reagent groups and at least two control analytes having two known amounts of the test analyte.

The processor 220 uses the adjusted control-light level for the reagent portion 100 in the first control channel 62 and the first known level of the control analyte 45 as the first point of the calibration curve for the test analyte 45. The processor 220 uses the adjusted control-light level for the reagent portion 100 in the second control channel 64 and the second known level of the control analyte 45 as the second point of the calibration curve for the test analyte 45.

The processor 220 uses the adjusted control-light level for the reagent portion 110 in the first control channel 62 and the first known level of the control analyte 47 as the first point of the calibration curve for the test analyte 47. The processor 220 uses the adjusted control-light level for the reagent portion 110 in the second control channel 64 and the second known level of the control analyte 47 as the second point of the calibration curve for the test analyte 47.

In an embodiment in which the test strip does not include a blank portion or a blank channel, the processor 220 operates on the unadjusted light levels. In such a case, the processor 220 uses the control-light level for the reagent portion 100 in the first control channel 62 and the first known level of the control analyte 45 as the first point of the calibration curve for the test analyte 45. The processor 220 uses the control-light level for the reagent portion 100 in the second control channel 64 and the second known level of the control analyte 45 as the second point of the calibration curve for the test analyte 45.

The processor 220 uses the control-light level for the reagent portion 110 in the first control channel 62 and the first known level of the control analyte 47 as the first point of the calibration curve for the test analyte 47. The processor 220 uses the control-light level for the reagent portion 110 in the second control channel 64 and the second known level of the control analyte 47 as the second point of the calibration curve for the test analyte 47.

In one implementation of this embodiment, there are more than two points for every calibration curve. In this case, there is an additional control channel in the test strip for each additional point on the calibration curve.

In another implementation of this embodiment, there are more than two calibration curves. For each additional calibration curve there is an additional reagent portion for a different reagent group in the test-sample channel and in each of the control channels.

At block 1010, the processor 220 determines an amount of the test analytes 47 in the test sample 40 from a placement of the test-light level for each test analyte 47 on the respective calibration curve for the control analytes 47.

The processor 200 determines if test light is detected for a test analyte 47, determines the test-light level for the detected test light and adjusts the test-light level by the reference-light level. Then the processor 200 determines where the adjusted light level is situated in the calibration curve for the test analyte.

Consider an exemplary case in which the test analyte 45 is reactive with the reagent group in the reagent portion 100 and the adjusted test-light level from the reagent portion 100 in the test-sample channel 60 is midway between two adjusted control-light levels in the calibration curve for the test analyte 45. In this case, the adjusted test-light level from the reagent portion 100 in the test-sample channel 60 is equal to $(CLL2-CLL1)/2+CLL1$, where $CLL1$ is the adjusted lower control-light level from the reagent portion 100 and $CLL2$ is the adjusted higher control-light level from the reagent portion 100. Then the amount of the test analyte 45 equals $(KA2-KA1)/2+KA1$, where $KA1$ is the first known amount of test analyte 45 in the first control channel 62 and KA2 is the second higher known amount of test analyte 45 in the second control channel 64.

To extend the exemplary case, the test analyte 47 is reactive with the reagent group in the reagent portion 110. The adjusted test-light level from the reagent portion 110 in the test-sample channel 60 is between the two adjusted control-light levels in the calibration curve for the test analyte 47. The two adjusted control-light levels have a difference $\Delta$CLL. The adjusted test-light level from the reagent portion 110 has a value that is a quarter of the difference $\Delta$CLL above the lower adjusted control-light level. In this case, the adjusted test-light level from the reagent portion 110 in the test-sample channel 60 is equal to (CLL4−CLL3)/4+CLL3, where CLL3 is the adjusted lower control-light level for the light from the reagent portion 110, CLL4 is the adjusted higher control-light level from the reagent portion 110 and $\Delta$CLL=CLL4−CLL3. Then the amount of the test analyte 47 equals (KA4−KA3)/2+KA3, where KA3 is the first known amount of test analyte 47 in the first control channel 62 and KA4 is the higher second known amount of test analyte 47 in the second control channel 64.

In this manner, the processor 220 determines reaction light levels correlated to the light detected from each of the reagent portions, determines a reference-light level correlated to the blank portion 300 or blank channel 66, forms calibration curves for respective reagent groups based on respective first reaction light levels and respective second reaction light levels and determines an amount of one or more test analytes 47 in the test sample 40 based on placements of third reaction light levels on respective calibration curves.

In one implementation of this embodiment, the processor 220 adjusts each reaction light level by the reference-light level, forms calibration curves for respective reagent groups based on respective first adjusted reaction light levels and respective second adjusted reaction light levels and determines an amount of one or more test analytes in the test sample based on placements of third adjusted reaction light levels on respective calibration curves.

FIG. 11 a cross-sectional side view of one embodiment of a system 9 to calibrate measurements of one or more test analytes from a test sample. FIGS. 12A-12C are cross-sectional front views of one embodiment of the system 9 to calibrate measurements of one or more test analytes from a test sample at different times during a calibration process. In this implementation of system 9, the test strip 32 is scanned through the system 9 after being exposed to the test sample 40, control sample 42 and control sample 44.

As shown in FIG. 11, the test strip 32 moves through the reader system 400 in the direction of the arrow 5. The reader system 400 includes the light source 250, a 3×1 linear array of lenses 211, a one-dimensional photodetector array 310, processor 220, memory 230 and display 234. The one-dimensional photodetector array 310 comprises photodetector elements 306, 301 and 304 positioned in a 3×1 linear array.

The light 260 from the light source 250 shines on a single row 105 or 106 of the reagent portions 100 or 110, respectively, (FIG. 1) of the test strip 32. At the moment of scanning shown in FIG. 12A, the light 260 is incident on the reagent portions 100 in the row 105 of the test strip 32 (FIG. 1). Reaction light 150 emitted from the reagent portion 100 of the first control channel 72 (FIG. 2) is focused by the linear array of lenses 211 onto the photodetector element 301 while reaction light 170 from the reagent portion 100 in the second control channel 74 (FIG. 2) is focused by the lens system 210 onto the photodetector element 304. The processor 220 is communicatively coupled to the one-dimensional photodetector array 310 and operates as described above to form a calibration curve 410 and to determine a presence and/or amount of a test analyte in the test sample 40. The calibration curve 410 is shown in the display 234 as a function of intensity (INT) and amount of test analyte. Exemplary text "0 TEST ANALYTE" indicates that there was no test analyte 45 (FIG. 4B) in the test sample 40.

The test strip 32 moves further through the reader system 400 so that, as shown in FIG. 12B, the light 260 is incident on the blank portion 300 in the test strip 32 (FIG. 1). The blank portion 300 transmits a portion of the light 260 as reference light 180 into the photodetector array 200. The reference light 180 and the processor 220 is focused by the linear array of lenses 211 onto the photodetector element 301 The processor 220 operates as described above to determine a reference-light level correlated to the reference light 180 detected from the blank portion 300 in the first control channel 72. The reference-light level is shown in the display 234 as a circle.

The test strip 32 moves further through the reader system 400 so that, as shown in FIG. 12C, the light 260 is incident on the reagent portions 110 in the row 106 of the test strip 32 (FIG. 1). As described above with reference to FIG. 2, reaction light 160 emitted from the reagent portion 110 of the test-sample channel 70. Reaction light 160 is focused by the linear array of lenses 211 onto the photodetector element 306. Reaction light 155 is emitted from the reagent portion 110 of the first control channel 72 and is focused by the linear array of lenses 211 onto the photodetector element 301. Reaction light 175 is emitted from the reagent portion 110 (FIG. 2) in the second control channel 74 is focused by the linear array of lenses 211 onto the photodetector element 304. The processor 220 is communicatively coupled to the one-dimensional photodetector array 310 and operates as described above to form a calibration curve 412 and to determine a presence and/or amount of a test analyte in the test sample 40. The calibration curve 412 is shown in the display 234. The test-light level is indicated as an asterisk (*) on the calibration curve 412 and the text "Z TEST ANALYTE" indicates that there was test analyte 47 in a amount "Z" in the test sample 40.

Other methods of scanning a test strip 32 across a one-dimensional photodetector array 310 are possible. In one implementation of this embodiment, the test strip 32 is manually scanned across a one-dimensional photodetector array 310. In another implementation of this embodiment, the test strip 32 is inserted into a slot in a reader system and is ejected from the same slot after all the reagent portions 100 and blank portions 300 of the test strip have been scanned by the light 260 and the reaction light was subsequently detected at the one-dimensional photodetector array 310 for each row 105 and 106 of reagent portions 100 and 110, respectively.

The methods and techniques described here may be implemented in digital electronic circuitry, or with a programmable processor (for example, a special-purpose processor or a general-purpose processor such as a computer) firmware, software, or in combinations of them. Apparatus embodying these techniques may include appropriate input and output devices, a programmable processor, and a storage medium tangibly embodying program instructions for execution by the programmable processor. A process embodying these techniques may be performed by a programmable processor executing a program of instructions to perform desired functions by operating on input data and generating appropriate output. The techniques may advantageously be implemented in one or more programs that are executable on a programmable system including at least one programmable processor coupled to receive data and instructions from, and to transmit data and instructions to, a data storage system, at least one input device, and at least one output device. Generally, a processor will receive instructions and data from a read-only memory and/or a random access memory.

Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and DVD disks. Any of the foregoing may be supplemented by, or incorporated in, specially-designed application-specific integrated circuits (ASICs).

A number of embodiments of the invention defined by the following claims have been described. Nevertheless, it will be understood that various modifications to the described embodiments may be made without departing from the spirit and scope of the claimed invention. Accordingly, other embodiments are within the scope of the following claims.

What is claimed is:

1. A system adapted to calibrate measurements of one or more test analytes in a test sample, the system comprising:
    a test strip comprising:
        a first channel configured to receive a test sample comprising an unknown amount of a first test analyte, the first channel comprising a first type of reagent group configured to bind with and generate reaction light when bound to the first test analyte, when present in the test sample, the first channel further comprising a second type of reagent group downstream of and different than the first type of reagent group, the second type of reagent group configured to bind with and generate reaction light when bound to a second test analyte different than the first test analyte; and
        a second channel configured to receive a control sample comprising a known amount of the first test analyte and a known amount of the second test analyte, the second channel comprising the first type of reagent group configured to bind with and generate reaction light when bound to the first test analyte in the control sample, the second channel further comprising the second type of reagent group downstream of and different than the first type of reagent group, the second type of reagent group configured to bind with and generate reaction light when bound to the second test analyte in the control sample, wherein the second channel comprises a blank portion having no reagent group, the blank portion positioned between the first type of reagent group and the second type of reagent group,
        wherein the first channel and the second channel are spatially separated from each other by a region in which there is no reagent group attached to a surface of the test strip to prevent liquid contact, and wherein the first type of reagent group in the first channel and the first type of reagent group in the second channel form a row that is perpendicular to the first channel and the second channel; and
    a processor configured to:
        determine light levels correlated to reaction light generated by the reagent groups in the first channel and the second channel, respectively; and
        determine a presence of the first test analyte in the test sample when the light level correlated to the reaction light generated by the first type of reagent group in the first channel is above the light level correlated to the reaction light generated by the first type of reagent group in the second channel.

2. The system of claim 1, wherein the test strip further comprises:
    a blank channel having no reagent groups.

3. The system of claim 1, in which the channels of the test strip are selected from the group consisting of a gel channel, a capillary channel, a glass channel, a paper channel, a wettable-fiber channel and combinations thereof.

4. A device adapted to calibrate measurements of one or more test analytes in a test sample, the device comprising:
    a sample tray having a first well configured to hold the test sample and a second well configured to hold a first control sample, the test sample comprising an unknown amount of a first test analyte, the first control sample comprising a known amount of the first test analyte and a known amount of a second test analyte different than the first test analyte;
    a test strip comprising:
        a first channel comprising a first type of reagent group configured to bind with and generate first test light when bound to the first test analyte, when present in the test sample, the first channel further comprising a second type of reagent group downstream of and different than the first type of reagent group, the second type of reagent group configured to bind with and generate second test light when bound to the second test analyte, the first channel positioned to wick the test sample from the first well; and
        a second channel comprising the first type of reagent group configured to bind with and generate first control light when bound to the first test analyte in the first control sample, the second channel further comprising the second type of reagent group downstream of and different than the first type of reagent group, the second type of reagent group configured to bind with and generate second control light when bound to the second test analyte in the first control sample, wherein the second channel comprises a blank portion having no reagent group, the blank portion positioned between the first type of reagent group and the second type of reagent group, the second channel positioned to wick the first control sample from the second well,
    wherein the first channel and the second channel are spatially separated from each other by a region in which there is no reagent group attached to a surface of the test strip to prevent liquid contact, and wherein the first type of reagent group in the first channel and the first type of reagent group in the second channel form a row that is perpendicular to the first channel and the second channel; and
    a processor configured to:
    determine light levels correlated to test light and control light generated by the reagent groups in the first channel and the second channel, respectively; and
    determine a presence of the first test analyte in the test sample when the light level correlated to the test light generated by the first type of reagent group in the first channel is above the light level correlated to the first control light generated by the first type of reagent group in the second channel.

5. The device of claim 4, wherein the test strip further comprises:
    a blank channel having no reagent groups.

6. The device of claim 4, in which the channels are selected from the group consisting of a gel channel, a capillary channel, a glass channel, a paper channel, a wettable-fiber channel and combinations thereof.

7. The system of claim 1, wherein the second type of reagent group in the first channel and the second type of reagent group in the second channel form a row that is perpendicular to the first channel and the second channel.

8. The device of claim 4, wherein the second type of reagent group in the first channel and the second type of reagent group in the second channel form a row that is perpendicular to the first channel and the second channel.

9. The system of claim 1, further comprising a third channel comprising the first type of reagent group configured to bind with and generate reaction light when bound to the first test analyte, the third channel further comprising the second type of reagent group downstream of and different than the first type of reagent group, the second type of reagent group configured to bind with and generate reaction light when bound to the second test analyte, wherein the third channel is adapted to receive a second control sample having a second known amount of the first test analyte and a second known amount of the second test analyte.

10. The device of claim 4, further comprising a third channel comprising the first type of reagent group configured to bind with and generate a third control light when bound to the first test analyte, the third channel further comprising the second type of reagent group downstream of and different than the first type of reagent group, the second type of reagent group configured to bind with and generate fourth control light when bound to the second test analyte, wherein the third channel is adapted to receive a second control sample having a second known amount of the first test analyte and a second known amount of the second test analyte.

11. The device of claim 4, wherein the processor is further configured to determine a reference light level correlated to the blank portion, and wherein the light levels correlated to the test light and the control light generated by the reagent groups is adjusted by the reference light level.

12. A device adapted to calibrate measurements of one or more test analytes in a test sample, the device comprising:
 a test strip comprising:
  a first channel configured to receive a test sample comprising an unknown amount of a first test analyte, the first channel comprising a first type of reagent group configured to bind with and generate first test light when bound to the first test analyte, when present in the test sample, the first channel further comprising a second type of reagent group downstream of and different than the first type of reagent group, the second type of reagent group configured to bind with and generate second test light when bound to a second test analyte different than the first test analyte;
  a second channel configured to receive a first control sample comprising a known amount of the first test analyte and a known amount of a second test analyte, the second channel comprising the first type of reagent group configured to bind with and generate first control light when bound to the first test analyte in the first control sample, the second channel further comprising the second type of reagent group downstream of and different than the first type of reagent group, the second type of reagent group configured to bind with and generate second control light when bound to the second test analyte in the first control sample, wherein the second channel comprises a blank portion having no reagent group, the blank portion positioned between the first type of reagent group and the second type of reagent group; and
  a third channel configured to receive a second control sample comprising a second known amount of the first test analyte and a second known amount of the second test analyte, the third channel comprising the first type of reagent group configured to bind with and generate a third control light when bound to the first test analyte, the third channel further comprising the second type of reagent group downstream of and different than the first type of reagent group, the second type of reagent group configured to bind with and generate fourth control light when bound to the second test analyte,
 wherein the first channel and the second channel are spatially separated from each other by a region in which there is no reagent group attached to a surface of the test strip to prevent liquid contact, and wherein the first type of reagent group in the first channel and the first type of reagent group in the second channel form a row that is perpendicular to the first channel and the second channel; and
 a processor configured to:
 determine a test light level correlated to test light generated by the first type of reagent group in the first channel;
 determine control light levels correlated to control light generated by the first type of reagent groups in the second and third channels;
 form a calibration curve based on the determined control light levels correlated to the first type of reagent groups in the second and third channels; and
 determine an amount of the first test analyte in the test sample based on placement of the determined test light level on the calibration curve.

13. The device of claim 12, wherein the second type of reagent group in the first channel, the second type of reagent group in the second channel, and the second type of reagent group in the third channel form a row that is perpendicular to the first channel, the second channel, and the third channel.

14. The device of claim 12, wherein the processor is further configured to determine a reference light level correlated to the blank portion, and wherein the light levels correlated to the test light and the control light generated by the reagent groups is adjusted by the reference light level.

* * * * *